US007214862B2

(12) United States Patent
Altosaar et al.

(10) Patent No.: US 7,214,862 B2
(45) Date of Patent: May 8, 2007

(54) PRODUCTION OF GM-CSF IN PLANTS

(76) Inventors: Illimar Altosaar, 950 Weston Drive, Ottawa, Ontario (CA) K1G 1X2; Ravinder Sardana, 2143 Valenceville Cres., Orleans, Ontario (CA) K4A 4K4; Anil Dudani, 56 Beamish Cres., Kanata, Ontario (CA) K2K 2R7; Peter Ganz, 1812 Thornecrest St., Gloucester, Ontario (CA) K1C 6K7; Eilleen Tackaberry, 325 Patricia Avenue, Ottawa, Ontario (CA) K1Z 6G7

( * ) Notice: Subject to any disclaimer, the term of this patent is extended or adjusted under 35 U.S.C. 154(b) by 0 days.

(21) Appl. No.: 10/723,083

(22) Filed: Nov. 26, 2003

(65) Prior Publication Data

US 2005/0050602 A1 Mar. 3, 2005

(30) Foreign Application Priority Data

Nov. 26, 2002 (CA) .................................... 2410702

(51) Int. Cl.
*A01H 5/00* (2006.01)

(52) U.S. Cl. ....................................... 800/320; 800/288

(58) Field of Classification Search ................ 800/288, 800/298, 320; 435/320.1
See application file for complete search history.

(56) References Cited

U.S. PATENT DOCUMENTS

| | | | |
|---|---|---|---|
| 5,677,474 A | 10/1997 | Rogers | |
| 5,889,189 A | 3/1999 | Rodriguez | |
| 6,288,302 B1 * | 9/2001 | Yu et al. | 800/287 |

OTHER PUBLICATIONS

Kaushansky et al., Hematopoietic activity of granulocyte/macrophage colony-stimulating factor is dependent upon two distinct regions of the molecule: Functional analysis based upon the activities of interspecies hybrid growth factors,PNAS,86:1213-1217 1989.*

Schnepf et al., *Bacillus thuringiensis* and Its Pesticidal Crystal Proteins, Microbiology and Molecular Biology Reviews, 62:775-806, 1998.*

Sardana et al., Biological activity of human granulocyte-macrophage colony stimulating factor is maintained in a fusion with seed glutelin peptide, Transgenic Research 11:521-531, 2002.*

Aoyama and Chua, "A glucocortocoid-mediated transcriptional induction system in transgenic plants," The Plant Journal vol. 11, No. 3, pp. 605-612 (1997).

Brandstatter, I. and Kieber, J.J., "Two genes with similarity to bacterial response regulators are rapidly and specifically induced by cytokinin in Arabidopsis," The Plant Cell vol. 10, pp. 1009-1019 (1998).

Burgess, A.W., et al. "Purification and properties of bacterially synthesized human granulocyte-macrophage colony stimulating factor," Blood, vol. 69, pp. 43-51 (1987).

Caddick et al, "An ethanol inducible gene switch for plants used to manipulate carbon metabolism," Nature Biotech. vol. 16, pp. 177-180 (1998).

Cantrell, M.A., et al. "Cloning, sequence, and expression of a human granulocyte/macrophage colony-stimulating factor," Proc Natl Acad Sci USA vol. 82, pp. 6250-6254 (1985).

Cheng, X et al., "Rice transformation by Agrobacterium infection," In: Recombinant Proteins from Plants: Production and Isolation of Clinically Useful Compounds. (eds. C. Cunningham and A.J.R. Porter) Humana Press, pp. 1-9 (1998).

Cheng et al., "Agrobacterium-transformed rice plants expressing synthetic CryIA(b) and CryIA(c) genes are highly toxic to striped stem borer and yellow stem borer," Proc Natl Acad Sci USA vol. 95, pp. 2767-2772 (1998).

Denecke et al, "Protein secretion in plant cells can occur via a default pathway," The Plant Cell, vol. 2, pp. 51-59 (1990).

Ernst, J.F., et al. "O-glycosylation and novel processing events during secretion of alpha-factor/GM-CSF fusions by *Saccharomyces cerevisiae*," Bio/Technology, vol. 5, pp. 831-834 (1987).

Gatz, C., "Chemical Control of Gene Expression," Ann. Rev. Plant Physiol. Plant Mol. Biol. vol. 48, pp. 89-108 (1997).

Jaeger, G.D, et al. "Boosting heteriogous protein production in transgenic dicotyledonous seeds using Phaseolus vulgaris regulatory sequences," Nature biotechnology, vol. 20, pp. 1265-1268 (2002).

James, E.A., et al., "Production and characterization of biologically active human GM-CSF secreted by genetically modified plant cells," Protein Express Purif, vol. 19, pp. 131-138 (2000).

Kakimoto, T., "CKI1, a histidine kinase homolog implicated in cytokinin signal transduction," Science, vol. 274, pp. 982-985 (1996).

Kaushansky, K., et al. "Role of carbohydrate in the function of human granulocyte-macrophage colony-stimulating factor," Biochemistry vol. 26, pp. 4861-4867 (1987).

Kitamura, T., et al., "Establishment and characterization of a unique human cell line that proliferates dependently on GM-CSF, IL-3, or erythropoietin," J Cellular Physiol, vol. 140, pp. 323-334 (1989).

Lee, F., et al. "Isolation of cDNA for a human granulocyte-macrophage colony-stimulating factor by functional expression in mammalian cells," Proc Natl Acad Sci USA vol. 82, pp. 4360-4364 (1985).

Metcalf, D, "Control of granulocytes and macrophages: Molecular, cellular, and clinical aspects," Science vol. 254, pp. 529-533 (1991).

Moonen, P., et al. "Increased biological activity of deglycosylated recombinant human granulocyte/macrophage colony-stimulating factor produced by yeast or animal cells," Proc Natl Acad Sci USA vol. 84, pp. 4428-4431 (1987).

(Continued)

*Primary Examiner*—Elizabeth F. McElwain
(74) *Attorney, Agent, or Firm*—Wilmer Cutler Pickering Hale and Dorr LLP

(57) ABSTRACT

The present invention discloses a method of producing granulocyte-macrophage colony stimulating factor (GM-CSF) in a plant comprising, transforming the plant with a genetic construct comprising a regulatory region functional in the plant, operably associated with a GM-CSF coding sequence, or a fragment or a derivative thereof, operably associated with a transcriptional terminator, and expressing the GM-CSF. Also disclosed are transgenic plants, seeds and cells comprising GM-CSF coding sequences and plant optimized GM-CSF coding sequences.

23 Claims, 6 Drawing Sheets

OTHER PUBLICATIONS

Murray et al., "Codon usage in plant genes," Nuc Acids Res. vol. 17, pp. 477-498 (1989).

Okamoto, M., et al. "Amplification and high-level expression for human granulocyte-macrophage colony-stimulating factor in human lymphoblastoid Namalwa cells," Bio/Technology, vol. 8, pp. 550-553 (1990).

Quesniaux and Jones. "Granulocyte-macrophage colony-stimulating factor," In: The Cytokine Handbook, (ed. Angus T.W.) Academic Press pp. 637-670 (1998).

Saalbach, I., et al. "High-level expression of a single-chain Fv fragment (scFv) antibody in transgenic pea seeds." J. Plant Physiol. vol. 158, pp. 529-533 (2001).

Salter et al, "Characterisation of the ethanol-inducible alc gene expression system for transgenic plants," The Plant Journal vol. 16, No. 1, pp. 127-132 (1998).

Sardana et al., "Construction and rapid testing of synthetic and modified toxin gene sequences CryIA (b&c) by expression in maize endosperm culture," Plant Cell Reports vol. 15, pp. 677-681 (1996).

Sardana R, et al. "Biological activity of human granulocyte macrophage colony stimulating factor is maintained in a fusion with seed glutelin peptide," Transgenic Research vol. 11, No. 5, pp. 521-531 (2002).

Stoger, E., et al. "Cereal crops as viable production and storage systems for pharmaceutical ScFv antibodies," Plant Mol Biol., vol. 42, pp. 583-590 (2000).

Tobias et al., "The N-end rule in bacteria," Science, vol. 254, pp. 1374-1377 (1991).

Ulmasov, T., et al., "Aux/IAA proteins repress expression of reporter genes containing natural and highly active synthetic auxin response elements," The Plant Cell, vol. 9, pp. 1963-1971 (1997).

Varshavsky, "The N-end rule: functions, mysteries, uses," Proc. Natl. Acad. Sci USA, vol. 93, pp. 12142-12149 (1996).

Vitale, A., et al., "The role of endoplasmic reticulum in protein synthesis, modification and intracellular transport," Journal of Experimental Botany, vol. 44, No. 266, pp. 1417-1444 (1993).

Wong, G.G., et al. "Human GM-CSF: Molecular cloning of the complementary DNA and purification of the natural and recombinant proteins," Science, vol. 228, pp. 810-815 (1985).

Zheng, Z., et al. "5'distal and proximal cis-acting regulator elements are required for developmental control of a rice seed storage protein glutelin gene," The Plant Journal, vol. 4, No. 2, pp. 357-366 (1993).

Zheng, Z.W., et al. "The bean seed storage protein beta-phaseolin is synthesized, processed, and accumulated in the vacuolar type-II protein bodies of transgenic rice endosperm," Plant Physiol vol. 109, pp. 777-786 (1995).

* cited by examiner

FIGURE 2
A
M
GM-CSF
NT
NO DNA
#1
#3
#4
#5
#6
GM-CSF
M
0.4 kb
B
1
NT
3
4
5
6
7
8
2.566 kb

```
GMCSF/Ori  .........ATGCACCACCACCACCACCACTCCTCCGGCATCGAGGGCCGCATGGCACCC   60
           ooooooooo|||||||||||||||||||||||||||||||||||||||||||||||o||o
GMCSF/Opti CGGCCCGGGATGCACCACCACCACCACCACTCCTCCGGCATCGAGGGCCGCATGGCGCCA

GMCSF/Ori  GCCCGGTCACCCAGCCCCAGCACGCAGCCCTGGGAGCATGTGAATGCCATCCAGGAGGCC  120
           ||o||oooo||o|||||ooo|||o|||||o||||||||o|||||o||o||||||||||||
GMCSF/Opti GCGCGCAGCCCGAGCCCGTCCACCCAGCCGTGGGAGCACGTGAACGCGATCCAGGAGGCC

GMCSF/Ori  CGGCGTCTCCTGAACCTGAGTAGAGACACTGCTGCTGAGATGAATGAAACAGTAGAAGTG  180
           ||oo|o|||||o|||||ooooo|o|||||o||o||o||||||||o||o||o||o||o|||
GMCSF/Opti CGCAGGCTCCTCAACCTCTCCCGCGACACCGCCGCCGAGATGAACGAGACCGTGGAGGTG

GMCSF/Ori  ATATCAGAAATGTTTGACCTCCAGGAGCCGACTTGCCTACAGACCCGCCTGGAGCTGTAC  240
           ||o||o||o|||||o||o||||||||||||||o|||||o|||||||||||o|||||||||
GMCSF/Opti ATCTCCGAGATGTTCGATCTCCAGGAGCCGACCTGCCTCCAGACCCGCCTCGAGCTGTAC

GMCSF/Ori  AAGCAGGGCCTGCGGGGCAGCCTCACCAAGCTCAAGGGCCCCTTGACCATGATGGCCAGC  300
           |||||||||||o||o||||||||||||||||||||||||||oo|o|||||||||||ooo|
GMCSF/Opti AAGCAGGGCCTCCGCGGCAGCCTCACCAAGCTCAAGGGCCCGCTCACCATGATGGCGTCC

GMCSF/Ori  CACTACAAGCAGCACTGCCCTCCAACCCCGGAAACTTCCTGTGCAACCCAGATTATCACC  360
           ||||||||||||||||||||o||o||||||||o||o|||||o||o||||||||o||||||
GMCSF/Opti CACTACAAGCAGCACTGCCCACCGACCCCGGAGACCTCCTGCGCCACCCAGATCATCACC

GMCSF/Ori  TTTGAAAGTTTCAAAGAGAACCTGAAGGACTTCCTGCTTGTCATCCCCTTTGACTGCTGG  420
           ||o||o||o|||||o||||||||o|||||||||||o||o||o|||||o||o|||||||||
GMCSF/Opti TTCGAGAGCTTCAAGGAGAACCTCAAGGACTTCCTCCTCGTGATCCCGTTCGACTGCTGG

GMCSF/Ori  GAGCCAGTCCAGGAGTGA....................  458
           |||||o||o|||||||||oooooooooooooooooooo
GMCSF/Opti GAGCCGGTGCAGGAGTGAGCTAGCGTCGACGCATGCCG
```

FIGURE 5

```
                *1
GMCSF/Ori   MHHHHHHSSGIEGRMAPARSPSPSTQPWEHVNAIQEARRLLNLSRDTAAEMNETVEV
            ||||||||||||||||||||||||||||||||||||||||||||||||||||||||||
GMCSF/Opti  MHHHHHHSSGIEGRMAPARSPSPSTQPWEHVNAIQEARRLLNLSRDTAAEMNETVEV

GMCSF/Ori  ISEMFDLQEPTCLQTRLELYKQGLRGSLTKLKGPLTMMASHYKQHCPPTPETSCATQIIT
           ||||||||||||||||||||||||||||||||||||||||||||||||||||||||||||
GMCSF/Opti ISEMFDLQEPTCLQTRLELYKQGLRGSLTKLKGPLTMMASHYKQHCPPTPETSCATQIIT

GMCSF/Ori  FESFKENLKDFLLVIPFDCWEPVQE    [SEQ ID NO:4]
           |||||||||||||||||||||||||
GMCSF/Opti FESFKENLKDFLLVIPFDCWEPVQE    [SEQ ID NO:2]
```

FIGURE 6

PRODUCTION OF GM-CSF IN PLANTS

This application claims priority to Canadian Patent Application No. 2,410,702, filed on Nov. 26, 2002.

FIELD OF THE INVENTION

The present invention relates to the production of GM-CSF in plants.

BACKGROUND OF THE INVENTION

At present, the majority of recombinant protein-based medicines are produced in mammalian cells or single cell organisms such as bacteria and yeast. However, the capital investment and operational costs associated with these systems are very high. For example, a mammalian cell-based manufacturing plant can cost upwards of $250 million. To achieve greater cost savings, and to address a capacity deficit in the global demand for recombinant protein-based pharmaceuticals, plants are being explored as alternative protein productions hosts (Giddings et al., 2000; Staub et al., 2000; Daniell et al., 2001; Walmsley et al., 2003). Different plant tissues such as leaves, seeds and tubers have been engineered for producing useful recombinant proteins (Vandekerckhove et al., 1989; Sijmons et al., 1990; Pen et al., 1992; Herbers et al., 1995; Ma et al., 1995; van Rooijen et al., 1995; Arakawa et al., 1998; Y Kusnadi et al., 1998; Zeitlin et al., 1998; Farran et al., 2002; Tackaberry et al., 1999). In a number of studies, tobacco has been used as a host plant but has some major drawbacks, including that tobacco is not a major food substance in a mammalian diet.

Granulocyte-macrophage colony stimulating factor (GM-CSF) is a cytokine of clinical importance. The mature GM-CSF is a polypeptide of 127 amino acid residues (Cantrell et al., 1985; Lee et al., 1985; Wong et al., 1985) and it regulates production and function of white blood cells (granulocytes and monocytes), which are important in fighting infections (Metcalf, 1991). GM-CSF is now an integral part of the clinical management for life-threatening neutropenia, the most common toxicity of cancer chemotherapy (Dale, 2002). Other oncology applications include treatment of febrile neutropenic conditions and support following bone marrow transplantation (Dale, 2002). Potential applications are also under evaluation in patients with pneumonia, Crohn's fistulas, diabetic foot infections and a variety of other infectious conditions including HIV-related opportunistic infections (Dale, 2002). The high cost of human GM-CSF in prior culture systems has placed practical limits on its widespread use (Dale, 2002). Previously, human GM-CSF has been produced by recombinant means in COS (Wong et al., 1985), yeast (Ernst et al., 1987) and Namalwa cells (Okamoto et al., 1990). GM-CSF has also been expressed in tobacco, but at very low levels (James et al., 2000; Sardana et al., 2002).

U.S. Pat. No. 5,677,474 (Rogers) teaches a method of producing foreign polypeptides in the seeds of cereal crops, including rice. Transformation of barley plants with a GUS reporter gene is disclosed. No transgenic plants containing GM-CSF were produced.

U.S. Pat. No. 5,889,189 (Rodriguez et al.) teaches a method of producing heterologous peptides in monocots including rice. Expression of a GUS reporter gene in transgenic rice seed is disclosed. No transgenic plants containing GM-CSF were produced.

James et al. (2000) used transformed tobacco cell suspensions to produce and secrete GM-CSF, which was then isolated from the growth medium. Yields were low (maximum of 250 microgram/L) and a complicated process of adding stabilizing proteins and increasing salt concentration of the growth media was necessary to enhance recovery of secreted GM-CSF. No transgenic cereal crops containing GM-CSF were produced.

Sardana et al. (2002) disclose the production of GM-CSF in transgenic tobacco seed. Yields were low with seed extracts containing recombinant human GM-CSF protein up to a level of 0.03% of total soluble protein. No transgenic cereal crops containing GM-CSF were produced.

SUMMARY OF THE INVENTION

The present invention relates to the production of GM-CSF in plants.

It is an object of the invention to provide an improved method of producing GM-CSF in plants.

According to an embodiment of the present invention, there is provided a method of producing granulocyte-macrophage colony stimulating factor (GM-CSF) in a cereal crop comprising growing a cereal crop that has a stably integrated genetic construct that includes a regulatory region functional in a cereal crop operably associated with GM-CSF coding sequence, or a fragment, or derivative thereof, operably associated with a transcriptional terminator.

According to the present invention there is provided a transgenic cereal crop plant comprising a stably integrated genetic construct that includes a regulatory region functional in a cereal crop operably associated with GM-CSF coding sequence, or a fragment, or derivative thereof, operably associated with a transcriptional terminator.

According to the present invention there is provided a genetic construct comprising a regulatory region functional in a cereal crop operably associated with a GM-CSF coding sequence optimized for expression in a cereal crop operably associated with a transcriptional terminator.

Cereal crops belong to the family Poaceae, and include graminoids or non-graminoids. In some instances cereal crops from the *Avena, Zea, Triticum, Secale* or *Hordeum* will be desirable. Commonly farmed cereal crops include, but are not limited to, rice, wheat, oats, rye, corn, sorghum, and barley. Each of the commonly farmed cereal crops can be classified into various cultivars. Rice (*Oryza sativa*), for example, includes a *japonica* cultivar and an *indica* cultivar. In a particularly preferred embodiment of the invention the cereal crop is *Oryza sativa, japonica* cv. Xiushui 11.

In an aspect of the present invention regulatory regions that are preferentially active within certain organs or tissues at specific developmental stages are contemplated. These regulatory regions may also be active in a developmentally regulated manner, or at a basal level in other organs or tissues within the plant as well. A number of regulatory regions of seed protein coding sequences have been identified and characterized. For example, glutelin (Gt), which represents the major reserve endosperm protein in rice seeds, is encoded by a small multigene family with subfamilies designated Gt1, Gt2, Gt3, etc. The glutelin regulatory regions have been shown to be preferentially active in seed/endosperm tissue.

In another aspect of the present invention the GM-CSF coding sequence is optimized for expression in a cereal crop. For example, the GM-CSF coding sequence is optimized for expression in rice, *japonica* cultivar. In a particularly preferred embodiment of the present invention the GM-CSF coding sequence is SEQ ID NO:1.

In another aspect of the present invention the GM-CSF coding sequence encodes an N-terminal methionine residue.

In another aspect of the present invention the GM-CSF coding sequence is operably linked to a signal sequence. For example, the signal sequence is the glutelin 1 signal sequence.

In another aspect of the present invention there is provided a method of producing granulocyte-macrophage colony stimulating factor (GM-CSF) in a plant comprising, transforming the plant with a genetic construct comprising a regulatory region functional in the plant, operably associated with a GM-CSF coding sequence, or a fragment or a derivative thereof, operably associated with a transcriptional terminator, and; expressing the GM-CSF.

In another embodiment, there is provided a method as defined above wherein the GM-CSF is human GM-CSF, a fragment or a derivative thereof. Preferably the GM-CSF exhibits between about 60% to 100%, preferably 80% to 100%, more preferably 95% to 100% of the activity of human GM-CSF.

The present invention also provides a method as defined above wherein the plant is a cereal plant, preferably rice. The rice may be, but is not limited to *japonica* cultivar.

The present invention also provides a method as defined above, wherein the genetic construct, or portion of the genetic construct is integrated into the genome of the plant. Alternatively, the construct may be extrachromosomal.

The present invention also provides a transgenic plant comprising a genetic construct comprising a regulatory region functional in the plant, operably associated with a plant optimized GM-CSF coding sequence or a fragment or a derivative thereof, operably associated with a transcriptional terminator.

The present invention also provides a genetic construct comprising a regulatory region functional in a plant, operably associated with a GM-CSF coding sequence optimized for expression in a plant, operably associated with a transcriptional terminator.

The transgenic plant may be, but is not limited to a cereal plant, preferably rice. However, other types of cereal plants are also contemplated. Further, the rice may be, but is not limited to *japonica* cultivar.

The present invention also provides a plant seed comprising the genetic construct comprising a regulatory region functional in a plant, operably associated with a GM-CSF coding sequence optimized for expression in a plant, operably associated with a transcriptional terminator.

The present invention also provides a plant cell comprising the genetic construct comprising a regulatory region functional in a plant, operably associated with a GM-CSF coding sequence optimized for expression in a plant, operably associated with a transcriptional terminator.

This summary of the invention does not necessarily describe all features of the invention.

BRIEF DESCRIPTION OF THE DRAWINGS

These and other features of the invention will become more apparent from the following description in which reference is made to the appended drawings wherein:

(FIG. 2A) PCR. Lane designations: M, 100-bp ladder as a marker; GM-CSF, positive control plasmid; NT, DNA from a non-transformed rice plant; NO DNA, negative control lacking template DNA; lanes marked as #1 to #6 represent six independent transgenic rice plants. (FIG. 2B): Southern blot. Lane 1 and 2: positive control as HindIII insert released from the construct shown in FIG. 1. Lanes 3–8: HindIII-cleaved genomic DNA from independent transgenic rice plants (#1-#6 respectively). NT refers to DNA from non-transformed rice plant.

FIG. 5 shows a DNA alignment between a non-optimized GM-CSF coding sequence (GMCSF/Ori; SEQ ID NO:3) and its derivative (SEQ ID NO:1) optimized for expression in rice (*O. sativa, japonica*). Sequence differences are indicated by "o".

FIG. 6 shows a protein alignment of the GM-CSF derivatives encoded by the GMCSF/Ori and GMCSF/Opti shown in FIG. 5. The protein sequences of GMCSF/Ori and GMCSF/Opti are identical. The N-terminal of the naturally occurring form of mature human GM-CSF is indicated by an arrow. An N-terminal methionine that is fused to the naturally occurring mature human GM-CSF is indicated by an asterisk.

DETAILED DESCRIPTION

Figure 1:
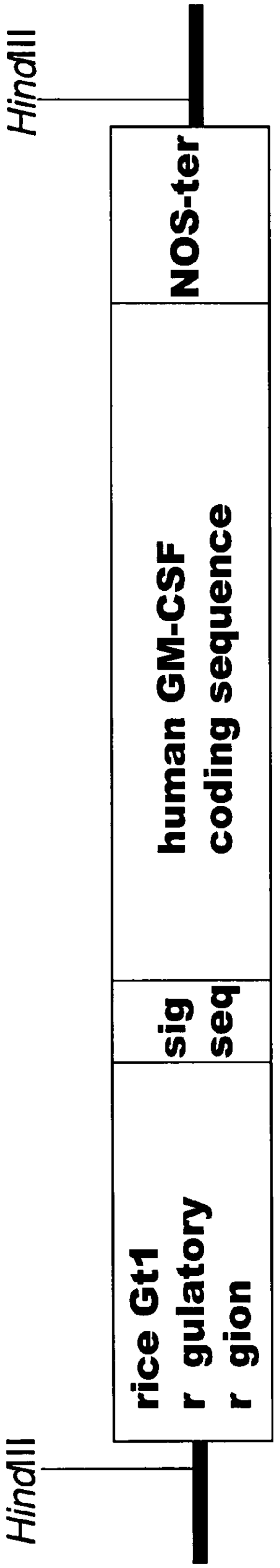
FIG. 1 shows a map of a genetic construct comprising a GM-CSF coding sequence operably associated with a Gt1 regulatory region in accordance with an embodiment of the present invention. The mature human GM-CSF sequence (384 bp) is fused in-frame with the rice glutelin signal sequence. The coding sequence is under the control of a 1.8 kb glutelin Gt1 promoter from rice. The NOS-TER fragment is 260 bp.

The following description is of a preferred embodiment.

GM-CSF has previously been produced in tobacco cells (James et al. 2000; Sardana et al., 2002). However, tobacco is inconvenient as an additive to a mammalian diet. Furthermore, GM-CSF yields from transgenic tobacco were low. The present invention provides an improved method of producing GM-CSF in plants.

The production of heterologous proteins in edible plants can simplify the subsequent processing required for preparation of medicament. In some cases, an edible transgenic plant containing a protein of interest may be added to an animal diet without any extraction of the protein from plant tissues. Alternatively, the heterologous protein may be purified or semi-purified from the plant.

Cereal crops form a natural part of the mammalian diet. Cereal crops belong to the family Poaceae, and include graminoids or non-graminoids. In some instances cereal crops from *Avena, Zea, Triticum, Secale* or *Hordeum* are desirable and contemplated by the present invention. Cereal crops of interest include, but are not limited to, rice, wheat, oats, rye, corn, sorghum, and barley. Rice and certain other cereal crops are self-pollinating, and therefore provide an advantage of self-containment of heterologous coding sequences of interest.

The present invention provides a method of producing GM-CSF comprising growing a cereal crop that has stably integrated a construct that includes a GM-CSF coding sequence.

An aspect of an embodiment of the present invention relates to transforming a plant with a genetic construct that comprises a GM-CSF, a fragment, or a derivative thereof in a cereal crop plant to produce a transformed cereal crop plant. With respect to coding sequence "fragment" means any 5', 3', or both 5' and 3' deletion. With respect to a protein or polypeptide, "fragment" means any N-terminal, C-terminal, or both N-terminal and C-terminal truncation. With respect to both coding sequence and encoded polypeptide, "derivative" means any addition, substitution, or deletion of nucleotide or amino acid residues, respectively. For example, a codon optimized GM-CSF coding sequence is a derivative of the naturally occurring GM-CSF coding sequence. As another example, a mature GM-CSF polypeptide having an N-terminal methionine residue is a derivative of the naturally occurring form that does not possess the N-terminal methionine. Preferably, the GM-CSF is a mammalian GM-CSF. More preferably, the GM-CSF is human GM-CSF (hGM-CSF). Even more preferably, the hGM-CSF is modified to optimize expression in cereal crop tissues. Therefore the present invention includes cereal crops, cereal crop cells or cereal crop seeds comprising a nucleotide sequence which encode GM-CSF, a fragment or a derivative thereof.

It is preferable that the GM-CSF, fragment or derivative thereof encoded by the plant exhibit substantially the same activity as natural or wild-type GM-CSF, preferably human GM-CSF. Preferably, it exhibits at least 50% of the activity, more preferably at least 80% and still more preferably at least 95% of the activity of human GM-CSF. It is also contemplated that the plant produced recombinant GM-CSF may exhibit a higher specific activity than that of wild type human GM-CSF. Various assays to measure activity of GM-CSF are known in the art, and any of these assays may be employed to compare the activity of plant produced recombinant GM-CSF with that of human GM-CSF.

The protein produced by the method of the present invention may comprise full-length mature GM-CSF or a fragment or derivative thereof. As will be appreciated by someone of skill in the art, an entire protein may not be required for the biological efficacy of EGF within a mammal, but rather, it may be possible that a smaller fragment of the protein may be used. As will also be recognized by the person skilled in the art, various derivatives such as altered glycosylation derivatives, or derivatives with additional N-terminal or C-terminal residues, or derivatives which alter the strength of association (Ka) or disassociation (Kd) between GM-CSF and its receptor, may also be employed without eliminating biological activity, and may even increase biological efficacy. An example of a GM-CSF produced by a cereal crop plant is full-length mature GM-CSF having about 127 amino acids. However, the actual length of the amino acid sequence may vary depending upon the signal sequences, added N-terminal or C-terminal amino acid residues, ER retention sequences, or protein purification tag sequences that may be added to the GM-CSF sequence. Any of such sequences, as would be known in the art, may be employed in the present invention.

The protein produced by the method of the present invention may be partially or completely purified from the plant. In addition, the protein may be formulated into a form for oral use or an injectable dosage form. Furthermore, the protein produced by the method of the present invention may be used for administration to a mammal, for example a human, in need thereof.

The protein produced by the method of the present invention, which comprises GM-CSF or fragments or derivatives thereof may have a variety of uses including, but not limited to the production of biologically active proteins for use as oral proteins, for systemic administration, for general research purposes, or combinations thereof. Further, the protein produced by the method of the present invention may be produced in large quantities in cereal crops, isolated and optionally purified at potentially reduced costs compared to other conventional methods of producing proteins such as, but not limited to, those which employ cell culture processes.

When preparing the genetic constructs and transgenic plants provided by the present invention several factors may be considered in order to optimize expression of heterologous coding sequences of interest. Increased expression of GM-CSF in cereal crops may be obtained by utilizing a modified or derivative nucleotide sequence. Examples of such sequence modifications include, but are not limited to, an altered G/C content to more closely approach that typically found in plants, and the removal of codons atypically found in plants commonly referred to as codon optimization. Other modifications include alteration of premature poly-A signals, mRNA destabilizing sequences and intron-like sequences. Preferential expression of GM-CSF in specific tissues, constitutively or at specific times is also contemplated. For example, seeds are known to store stable proteins for long periods of time and can accumulate high levels of proteins. Furthermore, strategies relating to targeting the protein encoded by a transgene to specific compartments within the cell, for example but not limited to the ER, can be adopted to address the problem of low levels of foreign protein expression in genetically transformed plants. At a subcellular level, organelles may also be targeted as required and may include targeting the transgene protein to the endoplasmic reticulum (ER), vacuole, apoplast, or chloroplast. Expression may also be increased through the use of translational fusions. For example, the transgene-encoded protein may be fused with a signal peptide that directs protein synthesis in plants into a desired cellular compartment, for example the ER. Optionally, the transgene fusion could comprise a second signal peptide that allows for retention of proteins in the ER or targeting of proteins to the vacuole. A non-limiting example of a signal sequence that may be used to target and retain the protein within the ER is the H/KDEL sequence (Schouten et al 1996, Plant Molec. Biol. 30, 781–793). Without wishing to be considered limiting in any manner, or bound by theory, replacing a secretory signal sequence with a plant secretory signal may also ensure targeting to the endoplasmic reticulum (Denecke et al 1990, Plant Cell 2, 51–59).

The choice of 3' and 5' untranslated regions operatively associated with a coding sequence are also factors which can affect expression levels. Generally, but not exclusively, transcriptional, translational, or both transcriptional and translational initiation regulatory regions will be found in 5' untranslated regions, while transcriptional termination signals are found in 3' untranslated regions. Regulatory regions and transcriptional terminators of the present invention will, at least, be functional in a cereal crop plant.

By "regulatory region" or "regulatory element" it is meant a portion of nucleic acid typically, but not always, upstream of the protein coding region of a gene, which may be comprised of either DNA or RNA, or both DNA and RNA. When a regulatory region is active, and in operative association with a coding sequence of interest, this may result in expression of the coding sequence of interest. A regulatory region may be spliced in vitro to be operatively associated with a coding sequence of interest. Alternatively, a coding sequence of interest may be integrated downstream of an endogenous regulatory region located within a plant genome. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. A number of regulatory regions of seed protein coding sequences have been identified and characterized. For example, glutelin (Gt), which represents the major reserve endosperm protein in rice seeds, is encoded by a small multigene family with subfamilies designated Gt1, Gt2, Gt3, etc. The glutelin promoters have been shown to be preferentially active in seed/endosperm tissue in controlling the expression of various reporter genes in transgenic plant systems, resulting in preferential expression in seed/endosperm tissue, and further expression that may be developmentally regulated. By "preferential expression in seeds" is meant that the encoded product of a coding sequence is, on average, present in higher levels in mature seeds than in other portions of the mature plant.

An inducible regulatory region is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory region to activate transcription, may be present in an inactive form which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352–358; which is incorporated by reference). Examples, of potential inducible promoters include, but not limited to, tetracycline-inducible promoter (Gatz, C., 1997, Ann. Rev. Plant Physiol. Plant Mol. Biol. 48, 89–108; which is incorporated by reference), steroid inducible promoter (Aoyama, T. and Chua, N. H., 1997, Plant J. 2, 397–404; which is incorporated by reference) and ethanol-inducible promoter (Salter, M. G., et al, 1998, Plant Journal 16, 127–132; Caddick, M. X., et al, 1998, Nature Biotech. 16, 177–180, which are incorporated by reference) cytokinin inducible IB6 and CKI1 genes (Brandstatter, I. and Kieber, J. J., 1998, Plant Cell 10, 1009–1019; Kakimoto, T., 1996, Science 274, 982–985; which are incorporated by reference) and the auxin inducible element, DR5 (Ulmasov, T., et al., 1997, Plant Cell 9, 1963–1971; which is incorporated by reference).

The coding sequence of the invention may be operatively associated with a suitable 3' untranslated region that is functional in plants. A 3' untranslated region refers to a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5'-AATAAA-3' although variations are not uncommon.

Examples of suitable 3' untranslated regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes and the small subunit of the ribulose-1,5-bisphosphate carboxylase (ssRUBISCO) gene.

Genetic constructs of the present invention can also include further enhancers, either translation or transcription enhancers, as may be required. These enhancer regions are well known to persons skilled in the art, and can include the ATG (methionine) initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the 5' region of the structural coding sequence, or may be derived from a source independent of the transcriptional initiation region or structural coding sequence. Translational initiation regions can be specifically selected and modified so as to increase translation of the mRNA.

In addition to enhancing translation of an mRNA, an N-terminal methionine residue may increase protein stability/yield. Tobias et al. (Science 254, 1374–1377 (1991)) reported protein half-lives of only two minutes when the following amino acids were present at the amino terminus: Arg, Lys, Phe, Trp, and Tyr. In a review of this phenomenon, termed the 'N-end rule', by Varshavsky (Proc. Natl. Acad. Sci USA, 93: 12142–49 (1996)), Glycine, Valine, and Methionine were identified as potential stabilizing residues that are common to all known N-end rules. However, such a result is not obtained for all proteins and thus secondary factors may also affect protein stability. Other derivatives of GM-CSF could confer added stability, improve yield, or provide a metabolic competitive advantage as compared to a wild-type plant or other recombinant plant transformed and expressing a gene of interest which is not GM-CSF. Further, other derivatives of GM-CSF may exhibit an altered, preferably increased strength of association between GM-CSF and its receptor. In still another embodiment contemplated herein, other derivatives of GM-CSF may promote upregulation or downregulation of the GM-CSF receptor or may enhance or inhibit receptor internalization when used or administered to a subject, such as, but not limited to a human.

The present invention provides a modified GM-CSF coding sequence that is codon optimized for expression in plants, preferably cereal crops. An example of a codon optimized GM-CSF sequence is shown in SEQ ID NO:1. By "codon optimized" is meant the selection of appropriate DNA nucleotides for use within a structural gene or fragment thereof that approaches codon usage within a plant. Therefore, an optimized gene or nucleic acid sequence refers to a gene in which the nucleotide sequence of a native or naturally occurring gene has been modified in order to utilize statistically-preferred or statistically-favored codons within a plant. The nucleotide sequence typically is examined at the DNA level and the coding region optimized for expression in plants determined using any suitable procedure, for example as described in Sardana et al. (1996, Plant Cell Reports 15:677–681). In this method, the standard deviation of codon usage, a measure of codon usage bias, may be calculated by first finding the squared proportional deviation of usage of each codon of the native GM-CSF gene relative to that of highly expressed plant genes, followed by a calculation of the average squared deviation. The formula used is:

$$SDCU = \sum_{n=1}^{N} [(Xn - Yn)/Yn]2/N$$

Where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477–498).

Another example of a method of codon optimization is based on the direct use, without performing any extra statistical calculations, of codon optimization tables such as those provided on-line at the Codon Usage Database through the NIAS (National Institute of Agrobiological Sciences) DNA bank in Japan (www.kazusa.or.jp/codon/). The Codon Usage Database contains codon usage tables for a number of different species, with each codon usage table having been statistically determined based on the data present in Genbank. For example, the following table (located at www.kazusa.or.jp/codon/cgi-bin/showcodon.cgi?species=Oryza+sativa+(japonica+cultivar-group)+[gbpln]) may be used for codon optimization of transgenes that are to be expressed in *japonica* cultivar rice plants:

| Oryza sativa (japonica cultivar-group) [gbpln]: 32630 CDS's (12783238 codons) fields: [triplet] [frequency: per thousand] ([number]) | | | | | | | |
|---|---|---|---|---|---|---|---|
| UUU | 13.6(173985) | UCU | 12.5(159540) | UAU | 10.3(131821) | UGU | 6.5( 82520) |
| UUC | 21.9(279329) | UCC | 15.6(199591) | UAC | 14.7(188349) | UGC | 12.1(154274) |
| UUA | 6.4(822284) | UCA | 11.8(150624) | UAA | 0.6( 8057) | UGA | 1.1( 14199) |
| UUG | 15.0(192153) | UCG | 12.0(153755) | UAG | 0.8( 10388) | UGG | 14.3(183072) |
| CUU | 14.9(190177) | CCU | 13.8(175845) | CAU | 11.6(148589) | CGU | 8.0(101835) |
| CUC | 24.2(309923) | CCC | 12.3(156817) | CAC | 13.9(178202) | CGC | 16.3(208778) |
| CUA | 8.0(102568) | CCA | 14.4(184035) | CAA | 14.3(183412) | CGA | 7.6( 96761) |
| CUG | 20.1(256688) | CCG | 17.7(226399) | CAG | 20.6(263543) | CGG | 14.1(180051) |
| AUU | 14.5(184754) | ACU | 11.0(140200) | AAU | 15.1(192829) | AGU | 8.8(112594) |
| AUC | 19.2(245629) | ACC | 15.0(191716) | AAC | 18.2(233034) | AGC | 15.4(197340) |
| AUA | 8.9(113169) | ACA | 11.7(148967) | AAA | 16.7(213264) | AGA | 10.9(138985) |
| AUG | 23.4(298881) | ACG | 11.6(148202) | AAG | 31.9(408318) | AGG | 15.8(202111) |
| GUU | 15.5(197654) | GCU | 19.6(250883) | GAU | 25.5(326196) | GGU | 14.9(189844) |
| GUC | 19.7(251434) | GCC | 30.1(385150) | GAC | 27.9(356336) | GGC | 28.5(364371) |
| GUA | 7.1( 90381) | GCA | 17.6(224608) | GAA | 22.6(289123) | GGA | 16.4(210234) |
| GUG | 23.8(304169) | GCG | 26.0(332493) | GAG | 38.6(493349) | GGG | 17.2(219456) |

Coding GC 55.04% 1st letter GC 58.27% 2nd letter GC 46.04% 3rd letter GC 60.81%

By using the above table to determine the most preferred or most favored codon(s) for each amino acid in a rice (*japonica* cultivar) plant, a naturally-occurring nucleotide sequence encoding a protein of interest can be codon optimized for expression in rice (*japonica* cultivar) by replacing codons that may have a low statistical incidence in the rice (*japonica* cultivar) genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring or native GM-CSF encoding nucleotide sequence may already, in advance of any modification, contain a number of codons that correspond to a statistically-favored codon in a particular plant species. Therefore, codon optimization of the native GM-CSF nucleotide sequence, may comprise determining which codons, within the native human GM-CSF nucleotide sequence, are not statistically-favored with regards to a particular plant, and modifying these codons in accordance with a codon usage table of the particular plant to produce a codon optimized derivative. The modified or derivative nucleotide sequence encoding GM-CSF may be comprised, 100 percent, of plant preferred codon sequences, while encoding a polypeptide with the same amino acid sequence as that produced by the native GM-CSF coding sequence. Alternatively, the modified nucleotide sequence encoding GM-CSF may only be partially comprised of plant preferred codon sequences with remaining codons retaining nucleotide sequences derived from the native GM-CSF coding sequence. A modified nucleotide sequence may be fully or partially optimized for plant codon usage provided that the protein encoded by the modified nucleotide sequence is produced at a level higher than the protein encoded by the corresponding naturally occurring or native gene. For example, the modified GM-CSF comprises from about 60% to about 100% codons optimized for plant expression. As another example, the modified GM-CSF comprises from 90% to 100% of codons optimized for plant expression.

A modified nucleotide sequence that is optimized for codon usage in a plant may possess a GC content that is similar to the GC content of nucleotide sequences that occur naturally and are expressed in that plant. However, the nucleotide sequence of a modified gene, that has only been partially optimized for codon usage in a plant, may be further modified so as to approach the GC content of nucleic acid sequences that occur naturally and are expressed in that plant. For example, a modified GM-CSF coding sequence, that is only partially optimized for codon usage in rice, may be further modified so as to approach the GC content of rice nucleotide sequences, while encoding a polypeptide with the same amino acid sequence as that produced by the native GM-CSF coding sequence. Furthermore, a native or naturally occurring gene could be optimized with respect to GC content without considering codon optimization. The modified nucleotide sequence of the present invention may be additionally optimised to create or eliminate restriction sites, or to eliminate potentially deleterious processing sites, such as potential polyadenylation sites or intron recognition sites, or mRNA destabilising sequences.

The present invention encompasses sequences that are similar or substantially identical to a coding sequence or modified coding sequence of GM-CSF. By "substantially identical" is meant any nucleotide sequence with similarity to the genetic sequence of GM-CSF, or a fragment or a derivative thereof. The term "substantially identical" can also be used to describe similarity of polypeptide sequences. For example, nucleotide sequences or polypeptide sequences that are greater than about 70%, preferably greater than about 80%, more preferably greater than about 70% identical to the GM-CSF coding sequence or the encoded polypeptide, respectively, and still retain GM-CSF activity are contemplated. To determine whether a nucleic acid exhibits similarity with the sequences presented herein, oligonucleotide alignment algorithms may be used, for example, but not limited to a BLAST (GenBank URL: www.Ncbi.ncbi.nlm.nih.gov/cgi-bin/BLAST/, using default parameters: Program: blastn; Database: nr; Expect 10; filter: default; Alignment: pairwise; Query genetic Codes: Standard(1)), BLAST2 (EMBL URL: www.embl-heidelberg.de/Services/index.html using default parameters: Matrix BLOSUM62; Filter: default, echofilter: on, Expect:10, cutoff: default; Strand: both; Descriptions: 50, Alignments: 50), or FASTA, search, using default parameters. Polypeptide alignment algorithms are also available, for example, without limitation, BLAST 2 Sequences (www.ncbi.nlm.nih.gov/blast/bl2seq/bl2.html, using default parameters Program: blastp; Matrix: BLOSUM62; Open gap (11) and extension gap (1) penalties; gap x_dropoff: 50; Expect 10; Word size: 3; filter: default).

An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. for at least 1 hour (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. for at least 1 hour (see Ausubel, et al. (eds), 1989, supra). Hybridization conditions may be modified in accordance with known methods depending on the sequence of interest (see Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.). Generally, but not wishing to be limiting, stringent conditions are selected to be about 5° C. lower than the thermal melting point for the specific sequence at a defined ionic strength and pH.

The present invention provides transgenic plants containing a genetic construct comprising a GM-CSF coding sequence. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, biolistics etc as would be known to those of skill in the art. For reviews of such techniques see for example Weissbach and Weissbach, *Methods for Plant Molecular Biology*, Academy Press, New York VIII, pp. 421–463 (1988); Geierson and Corey, *Plant Molecular Biology,* 2d Ed. (1988); and Miki and Iyer, *Fundamentals of Gene Transfer in Plants*. In *Plant Metabolism,* 2d Ed. DT. Dennis, D H Turpin, D D Lefebrve, D B Layzell (eds), Addison Wesly, Langmans Ltd. London, pp. 561–579 (1997).

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (*-glucuronidase), or luminescence, such as luciferase are useful.

Assembly of the genetic constructs of the present invention is performed using standard technology know in the art. The coding sequence of interest may be assembled enzymatically with appropriate regulatory regions and terminators, within a DNA vector, for example using PCR, or synthesized from chemically synthesized oligonucleotide duplex segments. The genetic construct, for example a DNA vector comprising the coding sequence of interest, is then transformed to plant genomes using methods known in the art. Alternatively, a functional genetic construct may be assembled in planta, for example a coding sequence operably associated with a translational initiation region may be integrated into a plant chromosome so as to become operably associated with an endogenous plant regulatory region. Proper integration of the coding sequence may be determined by any method known in the art, for example Southern analysis or PCR. Expression of the coding sequence may be determined using methods known within the art, for example Northern analysis, Western analysis or ELISA.

It is contemplated that a transgenic plant comprising a heterologous protein of interest may be administered to any animal, including humans, in a variety of ways depending upon the need and the situation. For example, if the protein is orally administered, the plant tissue may be harvested and directly feed to the animal, or the harvested tissue may be dried prior to feeding, or the animal may be permitted to graze on the plant with no prior harvest taking place. It is also considered within the scope of this invention for the harvested plant tissues to be provided as a food supplement within animal feed. If the plant tissue is being feed to an animal with little or not further processing it is preferred that the plant tissue being administered is edible. Furthermore, the protein obtained from the transgenic plant may be extracted prior to its use as a food supplement, in either a crude, partially purified, or purified form. In this latter case, the protein may be produced in either edible or non-edible plants. If transgenic rice plants expressing GM-CSF are being used, then administration using whole plant tissue could be as a feed or feed additive to humans or other animals.

Transgenic cereal crops expressing GM-CSF, for example in seed/endosperm can provide several advantages with respect to preparation and administration of pharmaceutical proteins. Rice seed endosperm-derived flour is an example of a food-grade platform that may be an optimal pipeline for producing pharmaceutical-grade proteins. Furthermore, production in seeds eliminates the need for immediate access to downstream processing facilities.

Alternatively, the protein produced by the method of the present invention may be partially or completely processed and purified from the plant and reformulated into a desired dosage form. The dosage form may comprise, but is not limited to an oral dosage form wherein the protein is dissolved, suspended or the like in a suitable excipient such as but not limited to water. In addition, the protein may be formulated into a dosage form that could be applied topically or could be administered by inhaler, or by injection either subcutaneously, into organs, or into circulation. An injectable dosage form may include other carriers that may function to enhance the activity of the protein. Any suitable carrier known in the art may be used. Also, the protein produced by the method of the present invention may be formulated for use in the production of a medicament. Again, the production of proteins in seed may be advantageous, even when further purification is contemplated. Production of pharmaceutical proteins in seed/endosperm offers one of the most appealing choices as seeds naturally store stable proteins for long periods of time and there are well-established seed fractionation procedures for major crops (Vandekerckhove et al., 1989; Saalbach et al., 2001; Stoger et al., 2000; Jaeger et al., 2002). Furthermore, the major proportion of seed proteins belong to a limited set of protein classes, which may simplify the purification procedure (Jaeger et al., 2002).

The present invention will be further illustrated in the following examples.

EXAMPLES

Example 1

Production of Biologically Active Human GM-CSF in Seeds of Transgenic Rice Plants Engineering the gene construct for the human GM-CSF coding sequence under the control of rice Gt1 promoter. A 1.8 kb Gt1 glutelin promoter from rice (Zheng et al., 1993) was used to control the expression of human GM-CSF mature coding sequence. To make the construct, standard DNA cloning and DNA amplifications techniques were followed (Sambrook et al., 1989). A plasmid containing the Gt1 promoter (Zheng et al., 1993) with associated 72 basepair Gt1 signal sequence was digested with NaeI enzyme that cleaved the plasmid right after the Gt1 signal sequence. After complete digestion, the digested plasmid DNA was dephosphorylated using alkaline phosphatase. The human GM-CSF coding DNA (without its human signal sequence) was amplified from the BBG12 plasmid using the polymerase chain reaction (PCR) and phosphorylated with T4 kinase. A ligation reaction was then set up that involved above prepared plasmid with Gt1 promoter and associated glutelin signal sequence as well as the GM-CSF DNA fragment. After transformation of bacterial cells with an aliquot from this ligation mixture, a transformed colony was identified with plasmid containing Gt1 promoter as well as glutelin signal sequence which was in-frame with the GM-CSF sequence. This plasmid was then cleaved at BamHI and HincII sites that were present on the 3' side of the stop codon of the GM-CSF sequence in order to incorporate a nopaline synthase terminator (NOS-TER) DNA fragment with a 5'BamHI site and a 3'blunt site. In this constructed plasmid, an EcoRI site was present on the 5' end of the Gt1 promoter and HindIII site was present on the 3' end of NOS terminator sequence. This particular plasmid was further modified to add a HindIII site on the 5' end of the Gt1 promoter by employing the use of an adaptor with a HindIII site. The HindIII fragment (FIG. 1) encompassing the complete construct was then cloned into the binary vector pCAMBIA 1301 (CAMBIA, Australia). This DNA vector was then transferred into the competent LBA4404 strain of *Agrobacterium.*

Transgenic rice plants and integration of human GM-CSF DNA in rice genome. The *Agrobacterium* cells containing the pCAMBIA/GM-CSF construct were used to transform vigorously growing rice calli. Transformed culture handling, callus induction from rice seeds (*Oryza sativa* cv. Xiushui 11), callus transformation with appropriate *Agrobacterium* cells, callus selection, maintenance and plant regeneration were essentially according to earlier methods (Cheng et al., 1998; Cheng et al., 1997). When plantlets reached about eight inches in height, and had a well-developed root system, they were transferred to pots of soil. Plants were grown to maturity in a controlled chamber at 28° C. with a relative humidity of 50–60%.

Figure 2:
FIG. 2 shows PCR products and a Southern blot on DNA from transgenic rice plants in accordance with a further embodiment of the present invention.

A total of six independent transgenic plants were regenerated from calli selected on hygromycin and chosen for further investigations. To ascertain the transgenic nature of the regenerated rice plants, DNA was extracted from leaf tissue. First, to detect the presence of insert in the DNA samples from selected rice plants, PCR reactions were performed using primers specific to human GM-CSF sequence coding sequence. A band of expected size was observed for all the six plants (FIG. 2A). The size of this band was identical to the one obtained for the positive control. No band was observed for the non-transgenic rice DNA sample. Similarly, for the negative control reaction without added DNA, no specific amplification was observed. For PCR, roughly 20–30 ng of rice genomic DNA was used as template for each sample. Primers were specific to the 5' and 3' termini of mature GM-CSF sequence. The DNA polymerase from New England Biolabs was used. The samples were subjected to one cycle of 95C for 5 minutes, 58C for 30 seconds and 72C for 90 seconds followed by 30 cycles of 95C for 60 seconds, 58C for 30 seconds and 72C for 90 seconds. In the final cycle, the extension time at 72C was extended to 6 minutes. Aliquots of PCR reactions were separated on 0.8% agarose gel stained with ethidium bromide.

Next, to verify the integration of the intact construct into the rice genome, purified rice genomic DNA from six PCR positive plants and a non-transformed control rice plant as well as positive control DNA were subjected to Southern analysis Rice genomic DNA was isolated and purified according to published protocol. For Southern blot, about 10 microgram of rice DNA was digested with HindIII. The digested DNA was separated on 0.8% agarose gel, denatured and transferred onto a nylon membrane. The membrane was probed with $^{32}$P-labelled fragment containing the GM-CSF sequence. The labeling was performed using a Ready to Go kit. (Pharmacia Biotech). Hybridizations were done at 42C in 50% formamide. The nylon membrane was washed at room temperature with 2×SSC, 0.1% SDS for 10 minutes. This was followed by two washings with 1×SSC, 0.1% SDS at 65C for 15 minutes, and a final wash at 65C with 0.4×SSC, 0.1% SDS for 15 minutes. The expected fragment of 2.566 kb was observed for plant # 1, 2, 4, 5 and 6 as well as for the positive control (FIG. 2B). An additional band was also present for plant # 1. For plant # 3, the observed bands were not of expected size. No bands were observed for the non-transformed (NT) rice plant.

Human GM-CSF-specific ELISA and Western blot analysis. To detect human GM-CSF protein in transgenic rice, extracts from seeds were made and assayed using a human GM-CSF-specific immunoassay. For ELISA, rice seeds (100 mg) were ground to powder and 100 microliter of extraction buffer (50 mM Tris pH 7.5, 50 mM NaCl, 1 mM EDTA, 1 mM PMSF, 1% 2-mercaptoethanol, 0.1% Triton X-100, 1% ascorbic acid and 1% polyvinylpyrrolidone) was added. The extracts were clarified by brief centrifugation (14000 g) at 4C. These clear extracts were used for quantifying GM-CSF using a Quantikine™ kit (R&D Systems) as described previously (Sardana et al., 2002). This kit provides for a human GM-CSF immunoassay based on a microplate precoated with a monoclonal antibody specific for human GM-CSF. All samples including standards were assayed in duplicate. Diluted aliquots of commercial GM-CSF and of seed extracts were dispensed into the wells of the microplate and incubated for two hours at room temperature. The unbound materials were washed away and GM-CSF conjugate was then added followed by another incubation at room temperature and transfer of substrate solution. The microplate reader set at 450 nm was used for determining the optical densities. For each assay, standard curves were generated utilizing purified *E. coli*-derived human GM-CSF, and the test sample values were derived from these. Protein content in samples was determined (Bradford, 1976). ELISA data (Table 1) showed that human GM-CSF accumulated to 1.2% and 1.3% of total soluble protein in rice seeds for plants # 1 and # 6, respectively, two of the three transgenic plants that were tested.

TABLE 1

| Plant ID | GM-CSF (microgram/mL) | Total Protein (mg/mL) | % GM-CSF of Total Soluble Protein |
|---|---|---|---|
| #1 | 28 | 2.2 | 1.3 |
| #5 | 5.6 | 2.3 | 0.24 |
| #6 | 28 | 2.4 | 1.2 |

Figure 3:
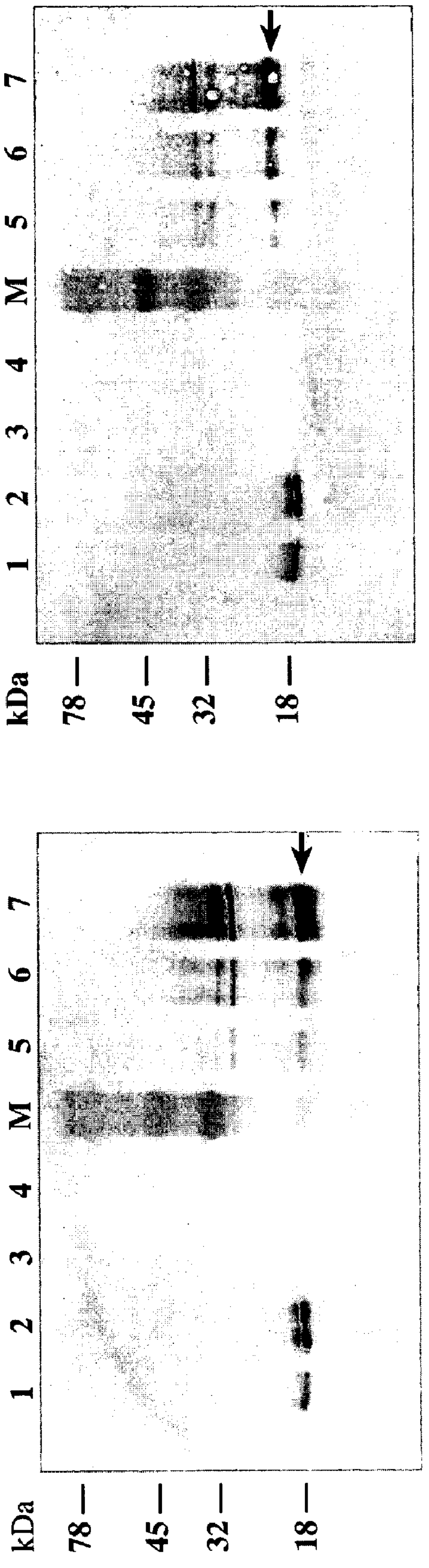
FIG. 3 shows a Western blot analysis detecting human GM-CSF protein in rice seed extracts in accordance with a further embodiment of the present invention. The blots for two independent transgenic rice plants are shown. Lane designations: M, prestained molecular weight marker; lanes 1 and 2, *E. coli*-derived commercial GM-CSF at two different concentrations; lanes 3 and 4, seed extract from a non-transformed rice plant; lanes 5–7, seed extracts at different concentrations from transgenic rice plants. The left panel is for transgenic rice plant # 1 and the right panel is for the transgenic rice plant # 6.

For further characterization, experiments involving Western blots were performed. The soluble protein extracts from seeds of rice plants # 1 and 6 and a control plant were subjected to denaturing polyacrylamide (15% SDS) gel electrophoresis. The proteins were transferred onto PVDF membranes. The blocking solution consisted of 1% BSA in Tris base saline (10 mM Tris pH 7.4, 150 mM NaCl). The membranes were probed with a 1:1000 dilution of a polyclonal rabbit antibody to GM-CSF (R&D Systems) followed by 1:7500 diluted alkaline phosphatase conjugated goat anti-rabbit IgG. Protein bands were visualized using the NBT/BCIP substrates (Fisher Scientific, Ottawa). A distinct band of approximately18 kDa was observed in lanes containing seed extracts from transgenic rice plants for both the blots (FIG. 3). The 18 kDa band from transgenic rice seed extract migrated to the same position on the gel as the corresponding *E. coli*-derived human GM-CSF. No bands were detected for the non-transformed control plants. In addition to the 18 kDa band, other bands that ranged in size from 19–44 kDA were also detected in the lanes containing the transgenic rice seed extracts.

Biological activity of the rice seed-expressed recombinant human GM-CSF. The biological activity of rice seed-derived human GM-CSF was tested using a human cell line, TF-1 (Kitamura et al., 1989) that grows only in the presence of medium supplemented with GM-CSF or other growth factors. TF-1 cells (Kitamura et al., 1989) were obtained from ATCC. These cells were grown as suspension cultures as described earlier (Sardana et al., 2002). Briefly, RPMI 1640 medium withl ng/mL *E. coli*-derived GM-CSF (R&D Systems) and fetal bovine serum (10%) was used. 1×PBS was used for washing the cells twice. Cells were resuspended in RPMI 1640 medium containing 10% fetal bovine serum at $2\times10^5$/L. Then $1\times10^5$ cells were dispensed to the wells of a 24-well tissue culture plate. Aliquots of 0.5 ml RPMI medium with 10% fetal bovine serum containing one of the following samples at a time were added to each of the wells: 1 ng/mL commercial GM-CSF (*E. coli*-derived), transgenic rice seed extract containing 1 ng of GM-CSF, seed extract from a non-transformed (NT) plant at equivalent protein concentration, seed protein extraction buffer (without mercaptoethanol). The dispensed 0.5 ml aliquots were from a stock solution that contained different seed extracts or commercial GM-CSF. All experiments were performed in quadruplicate and repeated at least twice under sterile conditions. The cell growth was monitored and live cells were counted using haemocytometry/trypan blue exclusion.

In summary, the TF-1 cells were grown in the presence or absence of commercially available *E. coli*-derived recombinant human GM-CSF or aliquots of rice seed extracts from transgenic and non-transformed control plants. Equal final concentrations of GM-CSF (whether positive control or seed-derived) were used. Viable TF-1 cells were quantified using vital staining (trypan blue exclusion).

Figure 4:
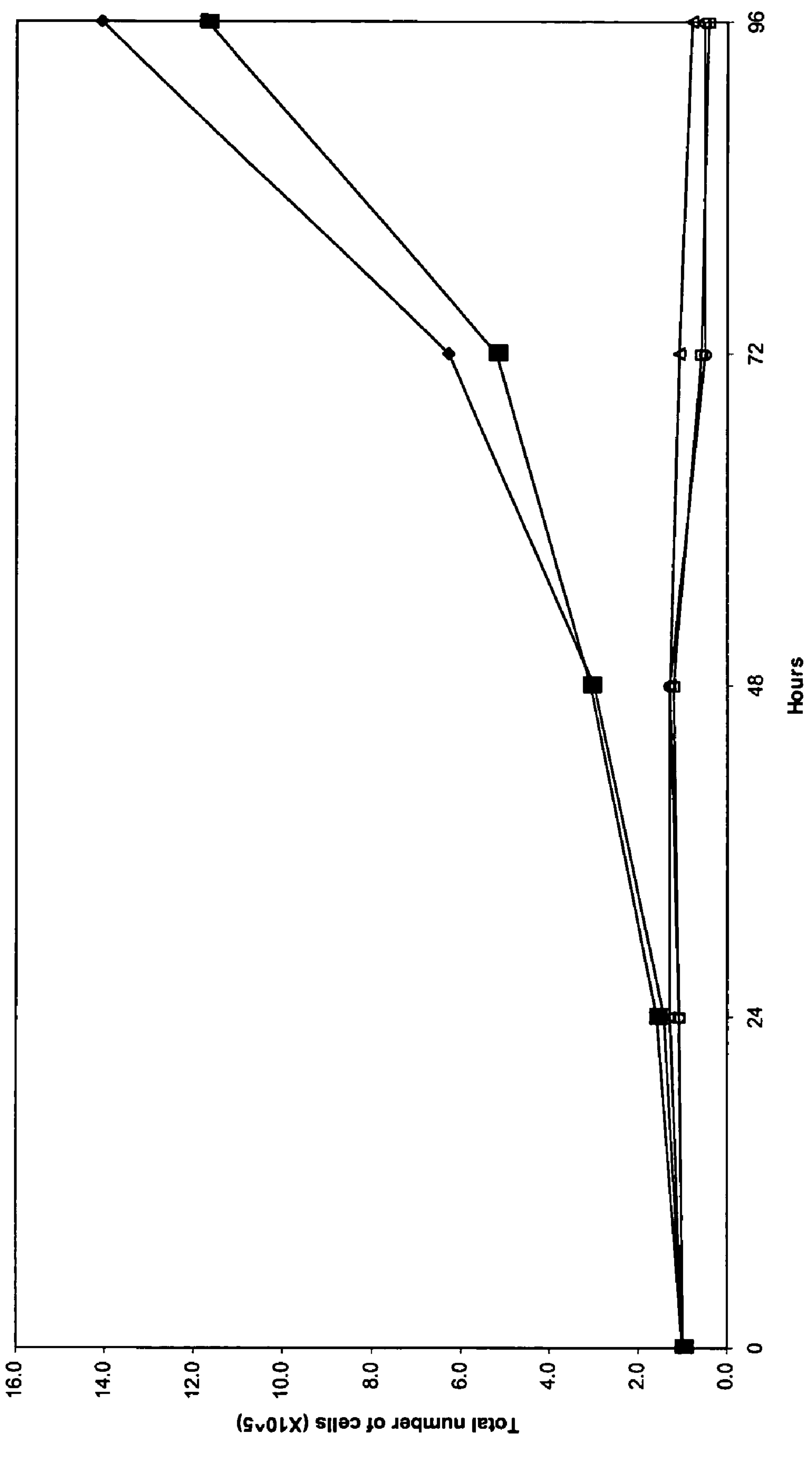
FIG. 4 shows biological activity of seed expressed human GM-CSF in accordance with a further embodiment of the present invention. Bioassays were done using TF-1 cells. The TF-1 cells grown as suspension cultures in RPMI 1640 medium were pipetted into duplicate wells ($1\times10^5$ cells/well) of a tissue culture plate. The cells were incubated in the absence or presence of seed extracts from transformed (#1 plant) and non-transformed (NT) plants, extraction buffer or *E. coli*. derived GM-CSF. Cell proliferation was determined using haemocytometry/trypan blue exclusion. Plot designations: (♦- - - ♦): Medium+GM-CSF; (x - - - x): Medium+Rice Extract; (Δ- - - Δ): Medium Alone; (□- - - □): Medium+NT Extract; (O - - - O): Medium+Extraction Buffer.

The results of these in vitro assays for GM-CSF biological activity are presented in FIG. 4. The assay medium alone (not supplemented with GM-CSF), the seed extract from non-transformed rice plants and the extraction buffer (EB) added to assay medium did not support proliferation of TF-1 cells over a period of 48 hours.

In contrast, when the seed extract from transgenic rice plant #1 was added to the medium, proliferation of TF-1 cells was observed after 48, 72 and 96 hours of incubation. The amount of proliferation was similar to that seen in the positive control (*E. coli*-derived human GM-CSF). As the data show, this rice seed extract resulted in about 6-fold increase in the number of TF-1 cells over the numbers obtained with medium alone. Similar results were observed with the seed extract of plant # 6 (data not shown).

Example 1 describes the production of a biologically active human recombinant protein, GM-CSF, in the seeds of transgenic rice plants. The human GM-CSF was put under control of the 1.8 kb Gt1 promoter from rice. A total of six independent transgenic rice plants were produced using *Agrobacterium*-mediated transformation procedures. Southern blot analysis suggested that five of these plants including plants #1 and #6 had no rearrangements in the GM-CSF construct, indicating that the construct is present in an intact form. The mature seeds from two of these plants were found to contain high levels of GM-CSF (approximately 1.3% of total soluble protein). This is more than 4-fold higher than the reported expression level in the seeds of tobacco (Sardana et al., 2002). Furthermore, even higher levels of GM-CSF in rice seeds may be achieved by employing a larger version of Gt1 promoter that has been shown to boost the production of phaseolin up to 4% in rice endosperm (Zheng et al., 1995).

The apparent molecular mass of unglycosylated GM-CSF is 15–18 kDa. Our Western blot analysis indicated that both *E. coli*-derived GM-CSF (unglycosylated form) and rice seed-derived GM-CSF migrated near the 18 kDa size marker. This suggests that the major 18 kDa form of seed-derived GM-CSF is likely unglycosylated. Other high molecular weight bands present at 19–44 kDa in both rice seeds extract may represent the glycosylated forms of GM-CSF. Furthermore, the presence of 18 kDa GM-CSF suggests that the rice glutelin signal peptide was cleaved from the human GM-CSF protein. The signal sequences of other seed storage proteins have been shown to be correctly processed in transgenic plants (Jaeger et al., 2002).

The implication about the presence of unglycosylated and glycosylated forms of GM-CSF in rice seed extracts is in agreement with similar findings reported on the expression of GM-CSF in yeast and mammalian cells. For example, human GM-CSF produced in yeast ranged in size up to 50 kDa (Ernst et al., 1987); and Namalwa cells producing GM-CSF showed protein ranging from 16 to 35 kDa (Okamoto et al., 1990) as determined by Western blot analysis. There are two potential N-glycosylation sites at Asn27 and Asn37 in the human GM-CSF protein (Cantrell et al., 1985; Lee et al., 1985; Wong et al., 1985). Most likely the smallest size molecules (16–18 kDa) have neither site glycosylated, the intermediate site has one site glycosylated and the largest size has both sites glycosylated (Okamoto et al., 1990). Various factors such as high-volume production conditions, cellular environment, protein structure and molecular interactions can affect the efficiency and state of glycosylation. As an example, the human and mouse GM-CSF produced in yeast are differentially glycosylated (Ernst et al., 1987). About 50% of the mouse GM-CSF is unglycosylated in yeast (Ernst et al., 1987). A seed storage protein is synthesized as a mixture of partially and fully-glycosylated protein in yeast (Vitale et al., 1993).

Regardless of glycosylation status of the rice seed-produced GM-CSF, the results of assays for biological activity of seed-produced GM-CSF indicated that the human protein is functional. This suggests that the protein produced in seed endosperm is maintained in an active conformation for interaction with the GM-CSF receptor. It is known that TF-1 cells (Kitamura et al., 1989) have specific receptors that bind to GM-CSF for proliferation.

Glycosylation status of rice-seed derived GM-CSF will be characterized, although glycosylation is not essential for biological activity of GM-CSF, either in vivo or in vitro (Burgess et al., 1987; Kaushansky et al., 1987; Moonen et al., 1987; Quesniaux et al., 1998). The core glycans are identical in mammalian and plant protein secretory systems, but plants have a different linkage with fucose (alpha 1–3 linked) and have xylose residues.

Biologically active recombinant human GM-CSF, a protein pharmaceutical with many applications in medicine and research, has been preferentially produced in the seeds of transgenic rice plants at high levels. As rice is a self-pollinated crop, it offers a particular attraction in terms of containment of the transgenes, in addition to providing advantages associated with producing protein-based medicines in seeds.

Example 2

Codon Optimization of GM-CSF

In modifying the GM-CSF coding sequence to optimize expression in plants several factors were considered:

Identify preferred codons for *Oryza sativa* (*japonica* cultivar);

Increase G/C content;

Match tRNA population of *Oryza sativa japonica* cultivar); and

Minimize secondary structure interactions.

An example of a codon optimized sequence is shown in FIG. 5 (bottom strand). The codon optimized sequence is aligned with a non-optimized GM-CSF. The G/C content of the optimized sequence is 66% compared to 40% G/C content for the non-optimized sequence. Both sequences encode a fusion polypeptide (see FIG. 6) comprising, in the direction of N-terminal to C-terminal:

a methionine residue;

a hexahistidine tag;

a 3 amino acid spacer;

a Factor X cleavage site;

a methionine residue; and the mature human GM-CSF sequence.

The fusion protein is designed such that cleavage at the Factor X site yields a mature human GM-CSF protein with an N-terminal methionine (indicated by an asterisk in FIG. 6). The N-terminal methionine can be important for increasing stability and yield. Also the N-terminal methionine may confer an altered strength of association between GM-CSF and its receptor, or it may alter the receptor number and/or internalization kinetics of the receptor.

A genetic construct comprising the optimized sequence was prepared in pGEM47. More specifically, the construct comprises, in the 5' to 3' direction:

a Glutelin 1 (Gt1) regulatory region;

a Glutelin 1 signal sequence;

the codon optimized sequence containing a sequence encoding the hexahistidine tag, spacer, and Factor X cleavage site; and an NOS terminator.

A SacI restriction fragment of pGEM47/His/GMCSF encompassing the complete genetic construct with optimized GM-CSF under control of the Gt1 regulatory region was then subcloned into a binary vector pCAMBIA1301 to produce pCAMBIA/His/GMCSFopti.

A pCAMBIA vector comprising the non-optimized coding sequence of the hexahistidine/GM-CSF fusion is also being produced and is being designated as pCAMBIA/His/GMCSFori.

pCAMBIA vectors identical to pCAMBIA/His/GMCSFopti and pCAMBIA/His/GMCSFori except that the mature GM-CSF coding sequence does not encode an N-terminal methionine are also being produced.

All four of the pCAMBIA vectors are being used to transform vigorously growing rice calli (*Oryza sativa, japonica* cv. Xiushui 11) according to methods described in Example 1.

Protein production and biological activity of GM-CSF (with or without N-terminal methionine) is being determined using methods described in Example 1.

All citations are hereby incorporated by reference.

REFERENCES

Arakawa, T., Yu, J., Chong, D. K. S., Hough, J., Engen, P. C. & Langridge, W. H. R. A plant based cholera toxin B subunit-insulin fusion protein protects against the development of autoimmune diabetes. Nature Biotechnology 16, 934–938 (1998).

Bradford, M. M. Rapid and quantitative method for quantification of microgram quantities of protein utilizing the principle of protein-dye binding. Anal Biochem 72, 248–252 (1976).

Burgess, A. W., Begley, C. G., Johnson, G. R., Lopez, A. F., Williamson, D. J., Mermod, J. J., Simpson, R. J., Schmitz, A. & DeLamarter, J. F. Purification and properties of bacterially synthesized human granulocyte-macrophage colony stimulating factor. Blood 69, 43–51 (1987).

Cantrell, M. A., Anderson, D., Cerretti, D. P., Price, V., Mckereghan, K., Tushinski, R. J., Mochizuki, D. Y., Larsen, A., Grabstein, K., Gillis, S. & Cosman, D. Cloning, sequence, and expression of a human granulocyte/macrophage colony-stimulating factor. Proc Natl Acad Sci USA 82, 6250–6254 (1985).

Cheng X, Sardana R and Altosaar I. Rice transformation by *Agrobacterium* infection. In: Recombinant Proteins from Plants: Production and isolation of clinically useful compounds. (eds. C. Cunningham and A. J. R. Porter) Humana Press, pp. 1–9 (1997).

Cheng, X. Y., Sardana, R., Kaplan, H. & Altosaar, I. *Agrobacterium*-transformed rice plants expressing synthetic CryIA(b) and CryIA(c) genes are highly toxic to striped stem borer and yellow stem borer. Proc Natl Acad Sci USA 95, 2767–2772(1998).

Dale, D. C. Colony-stimulating factors for the management of neutropenia in cancer patients. Drugs 62, (Suppl 1) 1–15 (2002).

Daniell, H., Streatfield, S. J. & Wycoff, K. Medical molecular farming: production of antibodies, biopharmaceuticals and edible vaccines in plants Trends Plant Sci. 2001 pp. 219–226.

Dorr, R. T. Clinical properties of yeast-derived versus *Escherichia coli*-derived granulocyte-macrophage colony-stimulating factor. Clin Ther 15, 19–29 (1993).

Ernst, J. F., Mermod, J. J., DeLamarter, J. F., Mattaliano, R. J. & Moonen, P. O-glycosylation and novel processing events during secretion of alpha-factor/GM-CSF fusions by *Saccharomyces cerevisiae*. Bio/Technology 5, 831–834 (1987).

Farran, I.; Sanchez-Serrano, J. J.; Medina, J. F.; Prieto, J.; Mingo-Castel, A. M., "Targeted expression of human serum albumin to potato tubers" Transgenic Res. 2002 pp. 337–346

Giddings, G., Allison, G., Brooks, D. & Carter, A. Transgenic plants as factories for biopharmaceuticals. Nat. Biotechnology 1151–1155 (2000).

Herbers, K., Wilke, I. & Sonnewald, U. A thermostable xylanase from *Clostridium thermocellum* expressed at high levels in the apoplast of transgenic tobacco has no detrimental effects and is easily purified. Bio/Technology 13, 63–66 (1995).

Hovgaard, D., Mortensen, B. T., Schifter, S. & Nissen, N. I. Comparative pharmacokinetics of single-dose administration of mammalian and bacterially derived recombinant human granulocyte-macrophage colony-stimulating factor. Eur J Haematol 50, 32–36 (1993).

Jaeger, G. D, Scheffer S, Jacobs, A, Zambre, Mzobell, O, Goossens, A, Depicker A and Angenon G (2002) Boosting heterlogous protein production in transgenic dicotyledonous seeds using *Phaseolus vulgaris* regulatory sequences. Nature biotechnology 20, 1265–1268

James, E. A., Changlin, W., Zeping, W., Reeves, R., Shin, J. H., Magnuson, N. S. & Lee, J. M. Production and characterization of biologically active human GM-CSF secreted by genetically modified plant cells. Protein Express Purif 19, 131–138 (2000).

Kaushansky, K., O'Hara, P. J., Hart, C. E., Forstrom, J. W. & Hagen, F. S. Role of carbohydrate in the function of human granulocyte-macrophage colony-stimulating factor. Biochemistry 26, 4861–4867 (1987).

Kitamura, T., Tange, T., Terasawa, T., Chiba, S., Kuwaki, T., Miyagawa, K., Piao, Y. F., Miyazono, K., Urabe, A. & Takaku, F. Establishment and characterization of a unique human cell line that proliferates dependently on GM-CSF, IL-3, or erythropoietin. J Cellular Physiol 140, 323–334 (1989).

Lee, F., Yokota, T., Otsuka, T., Gemmell, L., Larson, N., Luh, J., Arai, K. & Rennick, D. Isolation of cDNA for a human granulocyte-macrophage colony-stimulating factor by functional expression in mammalian cells. Proc Natl Acad Sci USA 82, 4360–4364 (1985).

Ma, J. K. C., Hiatt, A., Hein, M. D., Vine, N., Wang, F., Stabila, P., van Dolleweerd, C., Mostov, K. & Lehner, T. Generation and assembly of secretory antibodies in plants. Science 268, 716–719 (1995).

Metcalf, D. Control of granulocytes and macrophages: Molecular, cellular, and clinical aspects. Science 254, 529–533 (1991).

Moonen, P., Mermod, J. J., Ernst, J. F., Hirschi, M. & DeLamarter, J. F. Increased biological activity of deglycosylated recombinant human granulocyte/macrophage colony-stimulating factor produced by yeast or animal cells. Proc Natl Acad Sci USA 84, 4428–4431 (1987).

Okamoto, M., Nakayama, C., Nakai, M. & Yanagi, H. Amplification and high-level expression for human granulocyte-macrophage colony-stimulating factor in human lymphoblastoid Namalwa cells. Bio/Technology 8, 550–553 (1990).

Pen, J., Molendijk, L., Quax, W. J., Sijmons, P. C., van Ooyen, A. J. J., van den Elzen, P. J. M., Reitweld, K. & Hoekema, A. Production of active *Bacillus licheniformis* alpha-amylase in tobacco and its application in starch liquefaction. Bio/Technology 10, 292–296 (1992).

Quesniaux, V. J. F. & Jones, T. C. Granulocyte-macrophage colony-stimulating factor. In: Angus T (ed.), The Cytokine Handbook, (pp. 77–87) Academic Press (1998).

Robison, R. L. & Myers, L. A. Preclinical safety assessment of recombinant human GM-CSF in rhesus monkeys. Int Rev Exp Pathol 34A, 149–172 (1993).

Saalbach, I., Giersberg, M. & Conrad, U. High-level expression of a single-chain Fv fragment (scFv) antibody in transgenic pea seeds. J. Plant Physiol. 158, 529-533 (2001).

Sambrook, J., Fritsch, E. F. & Maniatis, T. Molecular cloning: A Laboratory Manual, 2nd edn. Cold Spring Harbor Laboratory Press, USA (1989).

Sardana R, Alli Z, Dudani A, Tackaberry E, Narayanan M, Panahi M, Ganz P and Altosaar I. Biological activity of human granulocyte macrophage colony stimulating factor is maintained in a fusion with seed glutelin peptide. Transgenic Research 11(5), 521–531 (2002).

Sijmons, P. C., Dekker, B. M. M., Schrammeijer, B., Verwoerd, T. C., van den Elzen, P. J. M. & Hoekema, A. Production of correctly processed human serum albumin in transgenic plants. Bio/Technology 8, 217–221 (1990).

Staub, J. M., Garcia, B., Graves, J., Hajdukiewicz, P. T., Hunter, P., Nehra, N., Paradkar, V., Schlittler, M., Carroll, J. A. & Spatola, L. "High-yield production of a human therapeutic protein in tobacco chloroplasts" Nat. Biotechnol. 333–338 (2000).

Stoger, E., Vaquero, C., Torres, E., Sack, M., Nicholson, L., Drossard, J., Williams, S., Keen, D., Perrin, Y., Christou, P. & Fischer, R. Cereal crops as viable production and storage systems for pharmaceutical ScFv antibodies. Plant Mol Biol 42, 583–590 (2000).

Tackaberry, E. S.; Dudani, A. K.; Prior, F.; Tocchi, M.; Sardana, R.; Altosaar, I.; Ganz, P. R., "Development of biopharmaceuticals in plant expression systems: cloning, expression and immunological reactivity of human cytomegalovirus glycoprotein B (UL55) in seeds of transgenic tobacco" Vaccine 1999 pp. 3020–3029.

van Rooijen, G. J. H. & Moloney, M. M. Plant seed oil-bodies as carriers for foreign proteins. Bio/Technology 13, 72–77 (1995).

Vandekerckhove, J., van Damme, J., van Lijsebettens, M., Botterman, J., De Block, M., Vandewiele, M., De Clercq, A., Leemans, J., Van Montagu, M. & Krebbers, E. Enkephalins produced in transgenic plants using modified 2S seed storage proteins. Bio/Technology 7, 929–932 (1989).

Vitale, A., Ceriotti, A. & Denecke, J. The role of endoplasmic reticulum in protein synthesis, modification and intracellular transport. J Experimental Botany 44, 1417–1444 (1993).

Walmsley, A. M. & Arntzen, C. Plant cell factories and mucosal vaccines. Current Opinion in Biotechnology 14, 145–150 (2003).

Wong, G. G., Witek, J. S., Temple, P. A., Wilkens, K. M., Leary, A. C., Luxenberg, D. P., Jones, S. S., Brown, E. L., Kay, R. M., Orr, E. C., Shoemaker, C., Golde, D. W., Kaufman, R. J., Hewick, R. M., Wang, E. A. & Clark, S. C. Human GM-CSF: Molecular cloning of the complementary DNA and purification of the natural and recombinant proteins. Science 228, 810–815 (1985).

Y Kusnadi, A., Hood, E., Witcher, D., Howard, J. & Nikolov, Z. Production and purification of two recombinant proteins from transgenic corn. Biotechnol Prog 14, 149–155 (1998).

Zeitlin, L., Olmsted, S. S., Moench, T. R., Co, M. S., Martinell, B. J., Paradkar, V. M., Russell, D. R., Queen, C., Cone, R. A. & Whaley, K. J. A humanized monoclonal antibody produced in transgenic plants for immunoprotection of the vagina against genital herpes. Nature Biotechnology 16, 1361–1364 (1998).

Zheng, Z., Kawagoe, Y., Xiao, S., Li, Z., Okita, T., Hau, T. L., Lin, A. & Murai, N. 5'distal and proximal cis-acting regulator elements are required for developmental control of a rice seed storage protein glutelin gene. Plant J 4, 357–366 (1993).

Zheng, Z. W., Sumi, K., Tanaka, K. & Murai, N. The bean seed storage protein beta-phaseolin is synthesized, processed, and accumulated in the vacuolar type-II protein bodies of transgenic rice endosperm. Plant Physiol 109, 777–786 (1995).

The present invention has been described with regard to one or more embodiments. However, it will be apparent to persons skilled in the art that a number of variations and modifications can be made without departing from the scope of the invention as defined in the claims.

What is claimed is:

1. A method of producing granulocyte-macrophage colony stimulating factor (GM-CSF) in a cereal crop comprising growing a cereal crop that has a stably integrated genetic construct that comprises a glutelin regulatory region operably associated with a GM-CSF coding sequence as set forth in SEQ ID NO: 1, or a fragment thereof that retains GM-CSF activity of supporting proliferation of TF-1 cells, operably associated with a transcriptional terminator.

2. The method according to claim 1, wherein the cereal crop is selected from the group consisting of: rice, wheat, oats, rye, corn, sorghum, and barley.

3. The method according to claim 1, wherein the GM-CSF coding sequence encodes an N-terminal methionine residue.

4. The method according to claim 2, wherein the cereal crop is rice.

5. The method according to claim 1, wherein the GM-CSF coding sequence is operably linked to a signal sequence.

6. The method according to claim 1, wherein the GM-CSF coding sequence is SEQ ID NO:1.

7. A transgenic cereal crop plant comprising a stably integrated genetic construct that comprises a glutelin regulatory region operably associated with a GM-CSF coding sequence as set forth in SEQ ID NO:1, or a fragment thereof that retains GM-CSF activity of supporting proliferation of TF-1 cells, operably associated with a transcriptional terminator.

8. The transgenic cereal crop according to claim 7, wherein the cereal crop is selected from the group consisting of: rice, wheat, oats, rye, corn, sorghum, and barley.

9. The transgenic cereal crop according to claim 7, wherein the GM-CSF coding sequence encodes an N-terminal methionine residue.

10. The transgenic cereal crop according to claim 8, wherein the cereal crop is rice, *japonica* cultivar.

11. The transgenic cereal crop according to claim 7, wherein the GM-CSF coding sequence is operably linked to a signal sequence.

12. The transgenic cereal crop according to claim 7, wherein the GM-CSF coding sequence is SEQ ID NO:1.

13. A genetic construct comprising a glutelin regulatory region operably associated with a GM-CSF coding sequence as set forth in SEQ ID NO:1, or a fragment thereof that retains GM-CSF activity of supporting proliferation of TF-1 cells, operably associated with a transcriptional terminator.

14. The genetic construct according to claim 13, wherein the cereal crop is selected from the group consisting of: rice, wheat, oats, rye, corn, sorghum, and barley.

15. The genetic construct according to claim 13, wherein the GM-CSF coding sequence encodes an N-terminal methionine residue.

16. The genetic construct according to claim 14, wherein the cereal crop is rice, *japonica* cultivar.

17. The genetic construct according to claim 13, wherein the GM-CSF coding sequence is operably linked to a signal sequence.

18. The genetic construct according to claim 13, wherein the GM-CSF coding sequence is SEQ ID NO:1.

19. An isolated nucleotide sequence comprising the sequence set-forth in SEQ IDNO:1.

20. A DNA vector comprising the genetic construct of claim 13.

21. A DNA vector comprising the isolated nucleotide sequence of claim 19.

22. A transgenic cereal crop plant comprising the genetic construct of claim 13.

23. A transgenic cereal crop plant comprising the isolated nucleotide sequence of claim 19.

* * * * *

SEQUENCE LISTING

```
<160> NUMBER OF SEQ ID NOS: 4

<210> SEQ ID NO 1
<211> LENGTH: 458
<212> TYPE: DNA
```

-continued

```
<213> ORGANISM: Homo sapiens
<220> FEATURE:
<221> NAME/KEY: CDS
<222> LOCATION: (10)..(438)
<223> OTHER INFORMATION:

<400> SEQUENCE: 1

cggcccggg atg cac cac cac cac cac cac tcc tcc ggc atc gag ggc cgc      51
          Met His His His His His His Ser Ser Gly Ile Glu Gly Arg
          1               5                   10

atg gcg cca gcg cgc agc ccg agc ccg tcc acc cag ccg tgg gag cac        99
Met Ala Pro Ala Arg Ser Pro Ser Pro Ser Thr Gln Pro Trp Glu His
15                  20                  25                  30

gtg aac gcg atc cag gag gcc cgc agg ctc ctc aac ctc tcc cgc gac       147
Val Asn Ala Ile Gln Glu Ala Arg Arg Leu Leu Asn Leu Ser Arg Asp
                35                  40                  45

acc gcc gcc gag atg aac gag acc gtg gag gtg atc tcc gag atg ttc       195
Thr Ala Ala Glu Met Asn Glu Thr Val Glu Val Ile Ser Glu Met Phe
            50                  55                  60

gat ctc cag gag ccg acc tgc ctc cag acc cgc ctc gag ctg tac aag       243
Asp Leu Gln Glu Pro Thr Cys Leu Gln Thr Arg Leu Glu Leu Tyr Lys
        65                  70                  75

cag ggc ctc cgc ggc agc ctc acc aag ctc aag ggc ccg ctc acc atg       291
Gln Gly Leu Arg Gly Ser Leu Thr Lys Leu Lys Gly Pro Leu Thr Met
    80                  85                  90

atg gcg tcc cac tac aag cag cac tgc cca ccg acc ccg gag acc tcc       339
Met Ala Ser His Tyr Lys Gln His Cys Pro Pro Thr Pro Glu Thr Ser
95                  100                 105                 110

tgc gcc acc cag atc atc acc ttc gag agc ttc aag gag aac ctc aag       387
Cys Ala Thr Gln Ile Ile Thr Phe Glu Ser Phe Lys Glu Asn Leu Lys
                115                 120                 125

gac ttc ctc ctc gtg atc ccg ttc gac tgc tgg gag ccg gtg cag gag       435
Asp Phe Leu Leu Val Ile Pro Phe Asp Cys Trp Glu Pro Val Gln Glu
            130                 135                 140

tga gctagcgtcg acgcatgccg                                             458


<210> SEQ ID NO 2
<211> LENGTH: 142
<212> TYPE: PRT
<213> ORGANISM: Homo sapiens

<400> SEQUENCE: 2

Met His His His His His His Ser Ser Gly Ile Glu Gly Arg Met Ala
1               5                   10                  15

Pro Ala Arg Ser Pro Ser Pro Ser Thr Gln Pro Trp Glu His Val Asn
            20                  25                  30

Ala Ile Gln Glu Ala Arg Arg Leu Leu Asn Leu Ser Arg Asp Thr Ala
        35                  40                  45

Ala Glu Met Asn Glu Thr Val Glu Val Ile Ser Glu Met Phe Asp Leu
    50                  55                  60

Gln Glu Pro Thr Cys Leu Gln Thr Arg Leu Glu Leu Tyr Lys Gln Gly
65                  70                  75                  80

Leu Arg Gly Ser Leu Thr Lys Leu Lys Gly Pro Leu Thr Met Met Ala
                85                  90                  95

Ser His Tyr Lys Gln His Cys Pro Pro Thr Pro Glu Thr Ser Cys Ala
            100                 105                 110

Thr Gln Ile Ile Thr Phe Glu Ser Phe Lys Glu Asn Leu Lys Asp Phe
        115                 120                 125

Leu Leu Val Ile Pro Phe Asp Cys Trp Glu Pro Val Gln Glu
```

-continued

```
    130                 135                 140


<210> SEQ ID NO 3
<211> LENGTH: 429
<212> TYPE: DNA
<213> ORGANISM: Homo sapiens
<220> FEATURE:
<221> NAME/KEY: CDS
<222> LOCATION: (1)..(429)
<223> OTHER INFORMATION:

<400> SEQUENCE: 3

atg cac cac cac cac cac cac tcc tcc ggc atc gag ggc cgc atg gca       48
Met His His His His His His Ser Ser Gly Ile Glu Gly Arg Met Ala
1               5                   10                  15

ccc gcc cgg tca ccc agc ccc agc acg cag ccc tgg gag cat gtg aat       96
Pro Ala Arg Ser Pro Ser Pro Ser Thr Gln Pro Trp Glu His Val Asn
            20                  25                  30

gcc atc cag gag gcc cgg cgt ctc ctg aac ctg agt aga gac act gct      144
Ala Ile Gln Glu Ala Arg Arg Leu Leu Asn Leu Ser Arg Asp Thr Ala
        35                  40                  45

gct gag atg aat gaa aca gta gaa gtg ata tca gaa atg ttt gac ctc      192
Ala Glu Met Asn Glu Thr Val Glu Val Ile Ser Glu Met Phe Asp Leu
    50                  55                  60

cag gag ccg act tgc cta cag acc cgc ctg gag ctg tac aag cag ggc      240
Gln Glu Pro Thr Cys Leu Gln Thr Arg Leu Glu Leu Tyr Lys Gln Gly
65                  70                  75                  80

ctg cgg ggc agc ctc acc aag ctc aag ggc ccc ttg acc atg atg gcc      288
Leu Arg Gly Ser Leu Thr Lys Leu Lys Gly Pro Leu Thr Met Met Ala
                85                  90                  95

agc cac tac aag cag cac tgc cct cca acc ccg gaa act tcc tgt gca      336
Ser His Tyr Lys Gln His Cys Pro Pro Thr Pro Glu Thr Ser Cys Ala
            100                 105                 110

acc cag att atc acc ttt gaa agt ttc aaa gag aac ctg aag gac ttc      384
Thr Gln Ile Ile Thr Phe Glu Ser Phe Lys Glu Asn Leu Lys Asp Phe
        115                 120                 125

ctg ctt gtc atc ccc ttt gac tgc tgg gag cca gtc cag gag tga          429
Leu Leu Val Ile Pro Phe Asp Cys Trp Glu Pro Val Gln Glu
    130                 135                 140


<210> SEQ ID NO 4
<211> LENGTH: 142
<212> TYPE: PRT
<213> ORGANISM: Homo sapiens

<400> SEQUENCE: 4

Met His His His His His His Ser Ser Gly Ile Glu Gly Arg Met Ala
1               5                   10                  15

Pro Ala Arg Ser Pro Ser Pro Ser Thr Gln Pro Trp Glu His Val Asn
            20                  25                  30

Ala Ile Gln Glu Ala Arg Arg Leu Leu Asn Leu Ser Arg Asp Thr Ala
        35                  40                  45

Ala Glu Met Asn Glu Thr Val Glu Val Ile Ser Glu Met Phe Asp Leu
    50                  55                  60

Gln Glu Pro Thr Cys Leu Gln Thr Arg Leu Glu Leu Tyr Lys Gln Gly
65                  70                  75                  80

Leu Arg Gly Ser Leu Thr Lys Leu Lys Gly Pro Leu Thr Met Met Ala
                85                  90                  95

Ser His Tyr Lys Gln His Cys Pro Pro Thr Pro Glu Thr Ser Cys Ala
            100                 105                 110
```

-continued

```
Thr Gln Ile Ile Thr Phe Glu Ser Phe Lys Glu Asn Leu Lys Asp Phe
        115                 120                 125

Leu Leu Val Ile Pro Phe Asp Cys Trp Glu Pro Val Gln Glu
    130                 135                 140
```